United States Patent
Iwaki et al.

(10) Patent No.: US 9,616,149 B2
(45) Date of Patent: Apr. 11, 2017

(54) LIQUID PRESENCE DETECTING DEVICE FUNCTIONING ALSO AS POWER SUPPLY, AND AIR IMPROVING DEVICE HAVING THE SAME

(71) Applicant: Hosiden Corporation, Yao-shi, Osaka (JP)

(72) Inventors: Toshikazu Iwaki, Yao (JP); Kimitake Sasaki, Yao (JP)

(73) Assignee: HOSIDEN CORPORATION, Yao-Shi (JP)

( * ) Notice: Subject to any disclaimer, the term of this patent is extended or adjusted under 35 U.S.C. 154(b) by 0 days.

(21) Appl. No.: 14/669,370

(22) Filed: Mar. 26, 2015

(65) Prior Publication Data

US 2015/0283281 A1    Oct. 8, 2015

(30) Foreign Application Priority Data

Apr. 2, 2014   (JP) .................................. 2014-076065

(51) Int. Cl.
*A61L 9/00* (2006.01)
*H01M 12/06* (2006.01)
(Continued)

(52) U.S. Cl.
CPC .............. *A61L 9/037* (2013.01); *A61L 9/122* (2013.01); *A61L 9/127* (2013.01); *G01F 23/00* (2013.01);
(Continued)

(58) Field of Classification Search
CPC ....................................................... A61L 9/037
(Continued)

(56) References Cited

U.S. PATENT DOCUMENTS

2008/0056691 A1* 3/2008 Wingo ................ A01M 1/2033
                                                                    392/395
2014/0062203 A1* 3/2014 Hirata ..................... H02J 9/061
                                                                    307/66

FOREIGN PATENT DOCUMENTS

EP          1787511         5/2007
JP          3768646         2/2006
(Continued)

OTHER PUBLICATIONS

Kaisheva et al., Mechanically rechargeable magnesium-air cells with NaCl-electrolyte, 2006, published in collection titled "New carbon based materials for electrochemical energy storage system" by Springer, pp. 106-116.*

(Continued)

*Primary Examiner* — Kevin Joyner
*Assistant Examiner* — Holly Mull
(74) *Attorney, Agent, or Firm* — Rankin, Hill & Clark LLP

(57) ABSTRACT

A liquid presence detecting device that has a simple and compact configuration, and which is high in efficiency, and an air improving device including the detecting device. The liquid presence detecting device includes a magnesium-air battery, and an electrical load. When liquid exists in a detection point, the magnesium-air battery operates (generates electricity), and, when liquid does not exist in the detection point, the operation of the magnesium-air battery stops. Therefore, the liquid presence detecting device detects the presence of liquid, and functions also as a power supply. The air improving device includes the liquid presence detecting device functioning also as a power supply, a device body, and an air improver which is detachably attached into the device body.

12 Claims, 10 Drawing Sheets

(51) Int. Cl.
    *A61L 9/03*         (2006.01)
    *G01N 27/22*       (2006.01)
    *G01F 23/26*       (2006.01)
    *A61L 9/12*         (2006.01)
    *G01F 23/00*       (2006.01)

(52) U.S. Cl.
    CPC ......... *G01F 23/263* (2013.01); *G01N 27/227* (2013.01)

(58) Field of Classification Search
    USPC ....................................................... 422/119
    See application file for complete search history.

(56) References Cited

FOREIGN PATENT DOCUMENTS

| WO | 2004/020005 | 3/2004 |
|---|---|---|
| WO | 2007/136795 | 11/2007 |

OTHER PUBLICATIONS

European Search Report dated Sep. 14, 2015, 6 pages.

\* cited by examiner

LIQUID PRESENCE DETECTING DEVICE FUNCTIONING ALSO AS POWER SUPPLY, AND AIR IMPROVING DEVICE HAVING THE SAME

TECHNICAL FIELD

The present invention relates to a liquid presence detecting device for detecting the presence of liquid such as water, and also to an air improving device having the same.

BACKGROUND ART

In liquid sensors for detecting the presence of liquid, such as a liquid level sensor and a liquid leakage sensor, conventionally, various detection methods have been used. In the contact type, the electrostatic capacitance method, the electro resistance method, and the like are used, and, in the non-contact type, the ultrasonic method, the optical method, and the like are employed. In each of such liquid sensors, the electrical difference between a state where liquid exists in a detection point, and that where liquid does not exist is obtained, and the presence of liquid is electrically detected. Such liquid sensors function as an electrical load which consumes power supplied from a power supply.

As an air improving device having such a liquid sensor, for example, Patent Literature 1 discloses a battery or AC power-driven evaporator in which aromatic liquid stored in a vessel is evaporated and discharged into a room so that the user can comfortably stay in the room. In the evaporator, when the aromatic liquid in the vessel is consumed, the aromatic effect is lost. Since the vessel is housed in a casing, it cannot be seen from the outside. Therefore, the evaporator includes a residual liquid sensor, and a situation where a small amount of the aromatic liquid remains in the vessel is informed to the user by using a lamp configured by a light-emitting diode.

The evaporator is configured so that a narrow tube is inserted into the vessel, the narrow tube is impregnated with the aromatic liquid to suck up the liquid by means of the capillary action, the sucked aromatic liquid is evaporated by a heater, and the evaporated liquid is discharged by the air current caused by a fan into the room. An aroma substance (simple aroma device) is known which is configured by aromatic liquid, a vessel containing the aromatic liquid, and a sucking wick that is inserted into the vessel, and that is impregnated with the aromatic liquid to suck up the liquid by means of the capillary action, and which causes the aromatic liquid sucked to an upper end portion of the sucking wick to vaporize. In such an aroma substance which does not require a power supply, a residual liquid sensor and lamp which are electrical loads are not used, and, in order to enable the user to visually check the remaining amount of the aromatic liquid in the vessel, each of the vessel, a printing film covering the vessel, and the like are made of a translucent material at the cost of degrees of freedom in design of the exterior, and the aromatic liquid is colored so that its visibility is improved.

PRIOR ART LITERATURE

Patent Literature

Patent Literature 1: Japanese Patent No. 3,768,646

SUMMARY OF THE INVENTION

Problems to be Solved by the Invention

Under a high temperature environment, the self discharge of a dry battery (a manganese battery or an alkaline battery) advances during storage (stoppage), and the capacity is reduced. Since lithium reacts vigorously with water, sufficient attention must be given in disposal of a used lithium battery.

In a liquid presence detecting device, a power supply is required as far as a conventional liquid sensor is used. This poses a large obstacle to a more simplified and compactified configuration of a liquid presence detecting device, and a higher efficiency.

It is an object of the invention to provide a liquid presence detecting device which has a simple and compact configuration, and which is high in efficiency, and an air improving device having the detecting device.

Means for Solving the Problems

In order to attain the object, the liquid presence detecting device functioning also as a power supply according to the invention includes a magnesium-air battery, and an electrical load which consumes power generated by the magnesium-air battery, the magnesium-air battery has an anode, a cathode, a liquid holder which is placed between these electrodes, and a liquid absorber which extends from the liquid holder to a point where a presence of liquid is detected, and, when the liquid exists in the detection point, the liquid absorber is soaked with the liquid, and the liquid is held as an electrolyte solution in the liquid holder, whereby the magnesium-air battery is caused to operate.

In a preferred mode of the liquid presence detecting device functioning also as a power supply according to the invention, the liquid is stored in a vessel, and a presence of the liquid stored in the vessel is detected.

The air improving device according to the invention includes the liquid presence detecting device functioning also as a power supply according to the invention, an device body, and an air improver which is detachably attached into the device body, the air improver has: air improving liquid; a vessel body which has an opening in an upper portion, and which stores the air improving liquid; a liquid sucking wick which is inserted into the vessel body from the opening, and which is impregnated with the air improving liquid to suck up the liquid by means of a capillary action; and a detachable cover member which passingly holds the liquid sucking wick in a central portion, which, when the cover member is attached to the opening of the vessel body to close the opening, insertingly holds the liquid sucking wick into the vessel body, and which is made of an insulating material, the magnesium-air battery has a cylindrical shape in which the anode is located inside the liquid holder, the cathode is located outside the liquid holder, and a liquid sucking wick through hole through which the liquid sucking wick is passable is formed, the magnesium-air battery is mounted on the cover member, and placed around the liquid sucking wick which is upward projected from the cover member, the liquid absorber is passed through a liquid absorber through hole which is disposed in the cover member and outside the liquid sucking wick, and extends to the detection point in the vessel body, and the electrical load is mounted on the device body, and, when the air improver is attached into the device body, electrically connected to the magnesium-air battery.

In a preferred mode of the air improving device according to the invention, the liquid absorber has a cylindrical shape, the liquid absorber through hole has an annular shape, a wick portion which is to be inserted from the opening into the vessel body is formed integrally with the cover member, the wick portion is configured by: a plurality of inner vertical bar portions which downward extend from a lower surface of the cover member and inside the liquid absorber through hole, and which are placed at predetermined intervals along a circumferential direction of the liquid absorber through hole; a plurality of outer vertical bar portions which downward extend from the lower surface of the cover member and outside the liquid absorber through hole, and which are placed at predetermined intervals along the circumferential direction of the liquid absorber through hole; and a coupling portion which couples together lower ends of the inner vertical bar portions and the outer vertical bar portions, portions of the cover member which are respectively inside and outside the liquid absorber through hole, and which are separated from each other by the annular liquid absorber through hole are integrated with each other to provide the cover member with an integral structure, and the cylindrical liquid absorber is received between the inner vertical bar portions and the outer vertical bar portions from the annular liquid absorber through hole, and placed around the liquid sucking wick.

In a preferred mode of the air improving device according to the invention, a lower liquid sucking wick through hole through which the liquid sucking wick is passable is disposed in a central portion of the coupling portion, the coupling portion is placed in a height position which is separated from the bottom surface of the vessel body, the liquid sucking wick is passed through the lower liquid sucking wick through hole to be in contact with the bottom surface of the vessel body, and a lower end of the liquid absorber butts against the coupling portion.

In a preferred mode of the air improving device according to the invention, an electrode case which has a liquid absorber extraction port and air intake ports for the anode, which houses the anode, the cathode, and the liquid holder, and which is made of an insulating material is disposed in the magnesium-air battery, the electrode case is configured by an upper case and a lower case, an electrode case top wall portion, an electrode case upper inner wall portion, and an electrode case upper outer wall portion are integrally formed in the upper case, the electrode case top wall portion has annular shape, and covers upper surfaces of the anode, the cathode, and the liquid holder, the electrode case upper inner wall portion has a cylindrical shape which downward extends from an inner peripheral edge of the electrode case top wall portion along an inner circumferential surface of the cathode, and which covers an upper portion of the inner circumferential surface of the cathode, the electrode case upper outer wall portion has a cylindrical shape which downward extends from an outer peripheral edge of the electrode case top wall portion along the outer circumferential surface of the anode, and which covers an upper portion of the outer circumferential surface of the anode, in the lower case, an electrode case bottom wall portion, an electrode case lower inner wall portion, and an electrode case lower outer wall portion are formed integrally with the cover member, the electrode case bottom wall portion is configured by a part of the cover member opposed to the lower surfaces of the anode and the cathode, covers the lower surfaces of the anode and the cathode, and has the liquid absorber through hole as the liquid absorber extraction port, the electrode case lower inner wall portion has a cylindrical shape which rises from an inner peripheral edge of the electrode case bottom wall portion along the inner circumferential surface of the cathode, and covers a lower portion of the inner circumferential surface of the cathode, the electrode case lower outer wall portion has a cylindrical shape which rises from an outer peripheral edge of the electrode case bottom wall portion along the outer circumferential surface of the anode, and covers an lower portion of the outer circumferential surface of the anode, the upper case and the lower case are integrated with each other in a state where the lower end of the electrode case upper inner wall portion, and the upper end of the electrode case lower inner wall portion are butted against each other, and the lower end of the electrode case upper outer wall portion, and the upper end of the electrode case lower outer wall portion are butted against each other, the electrode case passingly holds the liquid sucking wick inside the electrode case upper inner wall portion and the electrode case lower inner wall portion, and a plurality of air intake ports are disposed at predetermined intervals in the circumferential direction while extending over one or both of the electrode case upper outer wall portion and the electrode case lower outer wall portion.

In a preferred mode of the air improving device according to the invention, an anode terminal which is fixed in a state where one end side is in contact with the anode, and in a state where another end side is exposed from the upper surface of the upper case, and a cathode terminal which is fixed in a state where one end side is in contact with the cathode, and in a state where another end side is exposed from the upper surface of the upper case are disposed in the upper case, and an anode connection terminal which, when the air improver is mounted into the device body, is elastically contacted with the anode terminal, a cathode connection terminal which, when the air improver is mounted into the device body, is elastically contacted with the cathode terminal, and a control board to which the anode connection terminal, the cathode connection terminal, and the electrical load are electrically connected are disposed in the device body.

Effects of the Invention

According to the liquid presence detecting device functioning also as a power supply according to the invention, when liquid exists in the detection point, the magnesium-air battery operates (generates electricity), and, when liquid does not exist in the detection point, the operation of the magnesium-air battery stops. By using a magnesium-air battery, therefore, an electrical difference between a state where liquid exists in the detection point, and that where liquid does not exist can be captured, and the presence of liquid can be electrically detected. According to the liquid presence detecting device functioning also as a power supply according to the invention, namely, it is possible to provide a liquid presence detecting device which has a self-power generating function (the magnesium-air battery), which can electrically detect the presence of the liquid depending on the supply/stop of the self-generated power, which does not require an external power supply, which has a simple and compact configuration, and which is high in efficiency.

Since the magnesium-air battery is used, the device can be used even under a high temperature environment. The device can be disposed as general refuse.

The air improving device of the invention includes the liquid presence detecting device functioning also as a power supply according to the invention, and does not require an external power supply for the liquid presence detecting device. Therefore, it is possible to provide an air improving device which has a configuration that is correspondingly simple and compact, and which is high in efficiency.

In the case where a magnesium-air battery is to be mounted on the vessel body, the magnesium-air battery must be separately set in the vessel body in addition to the liquid sucking wick. In the air improving device of the invention, by contrast, the magnesium-air battery is mounted on the cover member. When the opening of the vessel body is closed by the cover member and the liquid sucking wick is set in the vessel body, therefore, also the magnesium-air battery is automatically set in the vessel body, and, even when the air improving device includes the liquid presence detecting device, the air improver can be easily assembled. In the air improving device of the invention, although the electric load is mounted on the device body, moreover, the electric load is electrically connected to the magnesium-air battery when the air improver is attached into the device body. When the air improver is attached into the device body to assemble the air improving device, therefore, also the liquid presence detecting device is automatically configured, and, although the liquid presence detecting device is included, the air improving device can be easily assembled. In the case where the magnesium-air battery is mounted on the vessel body, a liquid absorber through hole must be disposed in the vessel body in addition to the upper opening in order to allow the liquid absorber to extend to the detection point in the vessel body, and, even when a countermeasure is taken against leakage from the liquid absorber through hole, there is a possibility that leakage may occur during use. In the air improving device of the invention, by contrast, the magnesium-air battery is mounted on the cover member, and the liquid absorber is passed through the liquid absorber through hole which is disposed in the cover member and outside the liquid sucking wick, and extends to the detection point in the vessel body. Therefore, a configuration where a liquid absorber through hole is additionally disposed in the vessel body in addition to the upper opening, and a countermeasure against leakage from the liquid absorber through hole is taken is not necessary. Consequently, it is possible to prevent leakage from occurring during use. Since the magnesium-air battery is mounted on the cover member which is to be attached to the upper opening of the vessel body, the level difference between the detection point and the magnesium-air battery is ensured, and, when the air improving liquid is depleted from the state the air improving liquid exists in the detection point, extraction of the air improving liquid from the liquid holder, and drying of the liquid holder can be performed for a short time period. Therefore, the responsiveness of the liquid presence detecting device can be improved.

DESCRIPTION OF PREFERRED EMBODIMENTS

Hereinafter, the liquid presence detecting device functioning also as a power supply according to the invention will be described in detail by way of specific examples.

Embodiment 1

Figure 1:
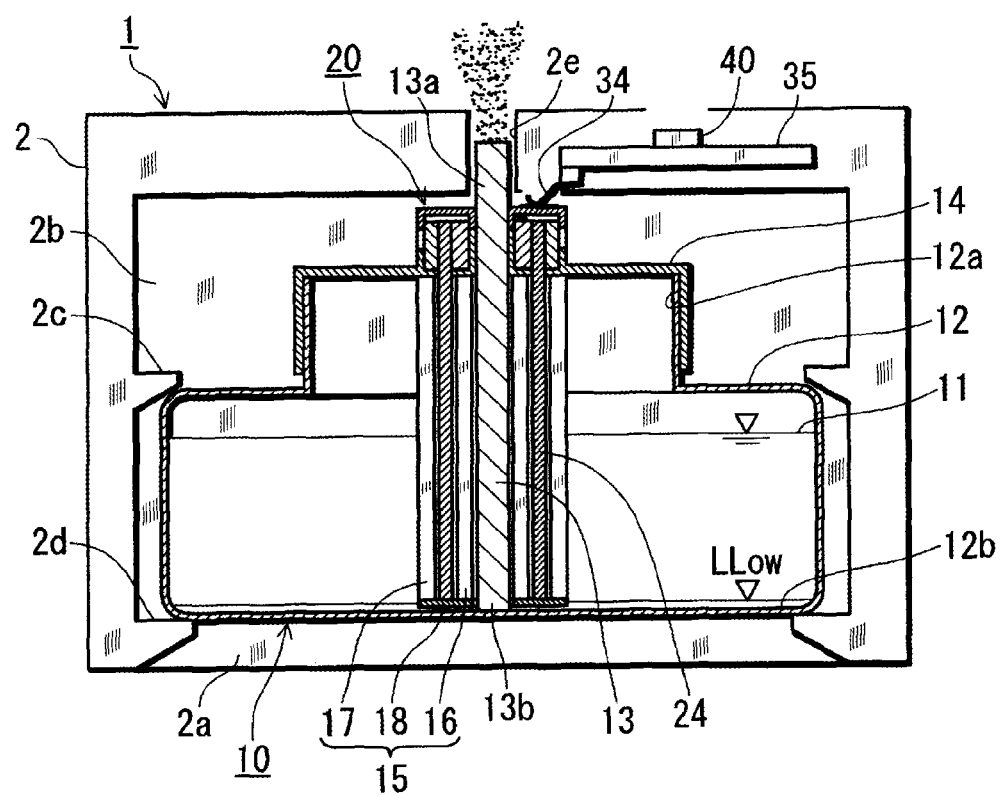
FIG. 1 is an overall configuration diagram of an air improving device which shows Embodiment 1 of the liquid presence detecting device functioning also as a power supply according to the invention.

FIG. 1 is an overall configuration diagram of an air improving device which shows Embodiment 1 of the liquid presence detecting device functioning also as a power supply according to the invention. The air improving device includes a device body 1, and an air improver 10 which is detachably attached into the device body 1.

The device body 1 has a device housing 2 made of an insulating synthetic resin. The air improver 10 is detachably attached into the device housing 2.

The device housing 2 has a ceiled cylindrical outer shape. An air improver insertion port 2a is formed in the bottom surface of the device housing 2. An air improver housing portion 2b is formed in the inner side (inside the device housing 2) of the air improver insertion port 2a. In order to vertically position the air improver 10 in the air improver housing portion 2b, a plurality of upper positioning projections 2c are formed at predetermined circumferential intervals on the peripheral side wall of the air improver housing portion 2b (vertically intermediate portion of the inner wall surface of the device housing 2), and a plurality of lower positioning projections 2d are formed at predetermined circumferential intervals on an edge portion of the air improver insertion port 2a (lower end portion of the inner wall surface of the device housing 2). A diffusion port 2e for the air improver 10 is formed in a central portion of a top wall portion of the device housing 2. In order to circumferentially position the air improver 10, recesses (key grooves) (not shown) are formed which extend respectively from a plurality of places of the edge portion of the air improver insertion port 2a so as to be continuous to the peripheral side wall of the air improver housing portion 2b.

The air improver 10 has: air improving liquid 11; a vessel body 12 which has an opening 12a in an upper portion, and which stores the air improving liquid 11; a liquid sucking wick 13 which is inserted into the vessel body 12 from the opening 12a, and which is impregnated with the air improving liquid 11 to suck up the liquid by means of the capillary action; and a detachable cover member 14 which passingly holds the liquid sucking wick 13 in a central portion, which, when the cover member is attached to the opening 12a of the vessel body 12 to close the opening 12a, insertingly holds the liquid sucking wick 13 into the vessel body 12, and which is made of an insulating synthetic resin. The air improver is configured so as to cause the air improving liquid 11 to vaporize from an upper end portion 13a of the liquid sucking wick 13 which is upward projected from the cover member 14. A lower end portion 13b of the liquid sucking wick 13 is in contact with the bottom surface 12b of the vessel body 12 so that the air improving liquid 11 in the vessel body 12 can be consumed up.

As the air improving liquid 11 of the air improver 10, for example, liquid such as water or a chemical solution according to the use of the air improving device such as aroma, odor elimination, deodorization, insect repellence, disinfestation, mildew prevention, sterilization, virus removal, dust removal, or humidification is used. The air improving liquid 11 is electrically conductive. As the vessel body 12, useful is a bottle which has the cylindrical opening 12a that is smaller in diameter than a trunk portion, and which is made of an insulating synthetic resin or insulating glass. In order to circumferentially position the air improver 10, projections (keys) (not shown) which are to be fitted to the recesses (not shown) of the device housing 2 are formed on the outer circumferential surface of the trunk portion of the vessel body 12. As the cover member 14, a cap which is to be screw-fixed to the opening 12a of the vessel body 12, and which is made of an insulating synthetic resin is used. The liquid sucking wick 13 is made of a material which can be impregnated with the air improving liquid 11 to suck up the liquid by means of the capillary action, such as natural fibers, synthetic fibers, or glass fibers, and has a thin rod-like shape.

In the air improver 10, at the timing when the vessel body 12 is filled with the air improving liquid 11 in a manufacturing plant, a simple cover member (cap) (not shown) which is used only for closing the opening 12a of the vessel body 12, and which is made of an insulating synthetic resin is attached to the opening 12a by means of a screw in order to prevent the air improving liquid 11 from vaporizing before the use. During use, the simple cover member is removed, the cover member 14 having the liquid sucking wick 13 is attached to the opening 12a of the vessel body 12 by means of a screw or the like, and the air improver is assembled into a use state shown in FIG. 1 in which the air improving liquid 11 can be vaporized from the upper end portion 13a of the liquid sucking wick 13. The air improver 10 which is assembled into the use state may be used also as an independent unit.

In the thus configured air improving device, after the air improver 10 is assembled into the use state, the air improver 10 is inserted into the air improver insertion port 2a of the device housing 2 from the upper end portion 13a of the liquid sucking wick 13, and then further pressed in a state where a shoulder portion of the vessel body 12 butts against the lower positioning projections 2d from the lower side.

Therefore, the lower positioning projections 2d are elastically deformed by the shoulder portion of the vessel body 12, the shoulder portion of the vessel body 12 butts against the upper positioning projections 2c while pushing the lower positioning projections 2d toward the outside of the trunk portion of the vessel body 12, and the air improver 10 is inserted to a full insertion position where further insertion is disabled, and attached to the air improver housing portion 2b of the device housing 2 so that the air improving device is assembled into the use state shown in FIG. 1.

When assembled into the use state, the air improving device is attached into the air improver housing portion 2b of the device housing 2, i.e., the device body 1 in the state where the lower positioning projections 2d are elastically restored as a result of passage of the vessel body 12, and engaged from the lower side with the outer peripheral edge of the bottom surface 12b of the vessel body 12, thereby preventing the air improver 10 from slipping off, the trunk portion of the vessel body 12 is interposed between the upper positioning projections 2c and the lower positioning projections 2d, thereby vertically positioning the air improver 10, the air improver 10 is circumferentially positioned by fitting between the recesses (not shown) of the device housing 2 and the projections (not shown) of the vessel body 12, and the upper end portion 13a of the liquid sucking wick 13 is inserted into the diffusion port 2e of the device housing 2.

In the case where the air improver 10 for deodorization and aroma is attached into the device body 1, and the air improving device (deodorizing aromatic device) which is assembled into the use state is placed on a horizontal plane in a room or the like and then used, for example, the air improving device causes the air improving liquid 11 for deodorization and aroma impregnated in the liquid sucking wick 13 to be sucked to an upper end portion of the liquid sucking wick 13 by means of the capillary action, and to be vaporized from the upper end portion of the liquid sucking wick 13, so that deodorizing and aromatic components are diffused from the diffusion port 2e of the device housing 2 into the room, whereby deodorizing and aromatic effects are attained. When the air improving liquid 11 in the vessel body 12 vanishes, the deodorizing and aromatic effects disappear. When the used air improver 10 is removed through the air improver insertion port 2a of the device housing 2, and a new air improver 10 for deodorization and aroma in which the air improving liquid 11 is stored in the vessel body 12 is attached, the deodorizing and aromatic effects are again attained.

The air improving device includes the liquid presence detecting device functioning also as a power supply according to the invention. The liquid presence detecting device functioning also as a power supply according to the invention includes a magnesium-air battery 20, and an electrical load 40 which consumes power generated by the magnesium-air battery 20. The magnesium-air battery 20 has an anode 21, a cathode 22, a liquid holder 23 which is placed between these electrodes, and a liquid absorber 24 which extends from the liquid holder 23 to a point where a presence of liquid is detected. When the liquid exists in the detection point, the liquid absorber 24 is soaked with the liquid, and the liquid is held as an electrolyte solution in the liquid holder 23, whereby the magnesium-air battery 20 is caused to operate, and the electrical load 40 is caused to operate. By contrast, when liquid does not exist in the detection point, the liquid holder 23 is kept to a dry state, whereby the magnesium-air battery 20 is caused to stop, and the electrical load 40 stops to operate.

Figure 2:
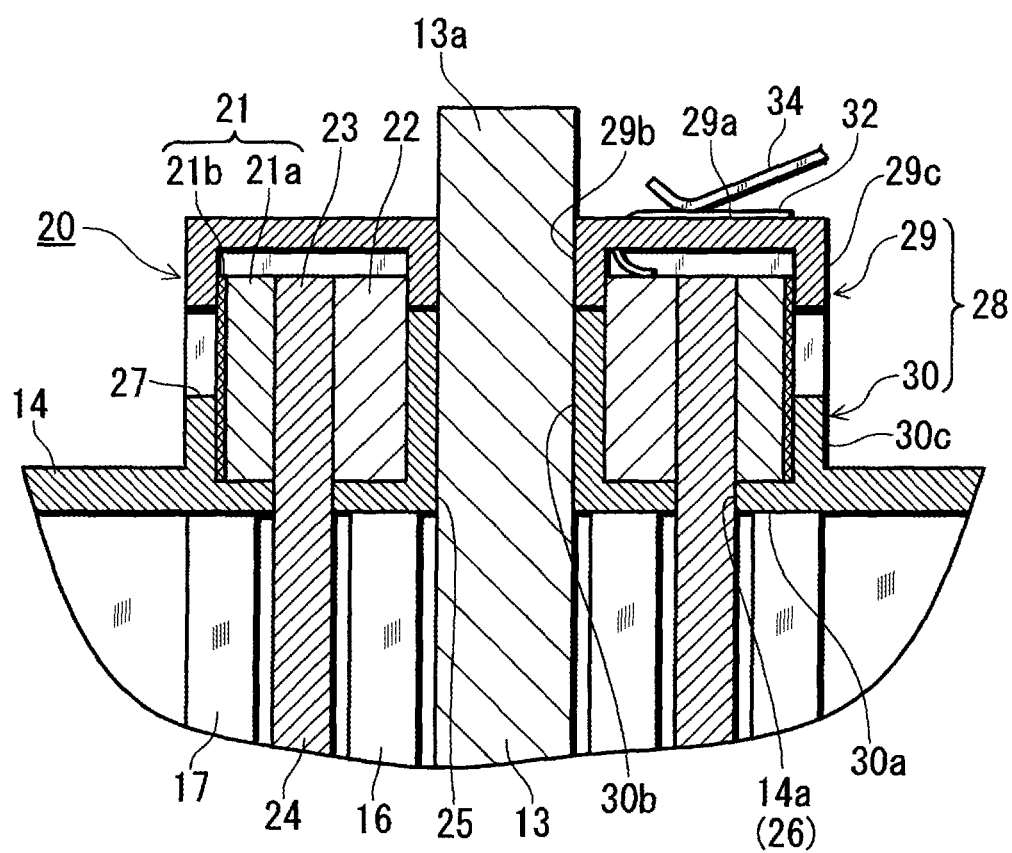
FIG. 2 is a side sectional view of a magnesium-air battery.
Figure 3:
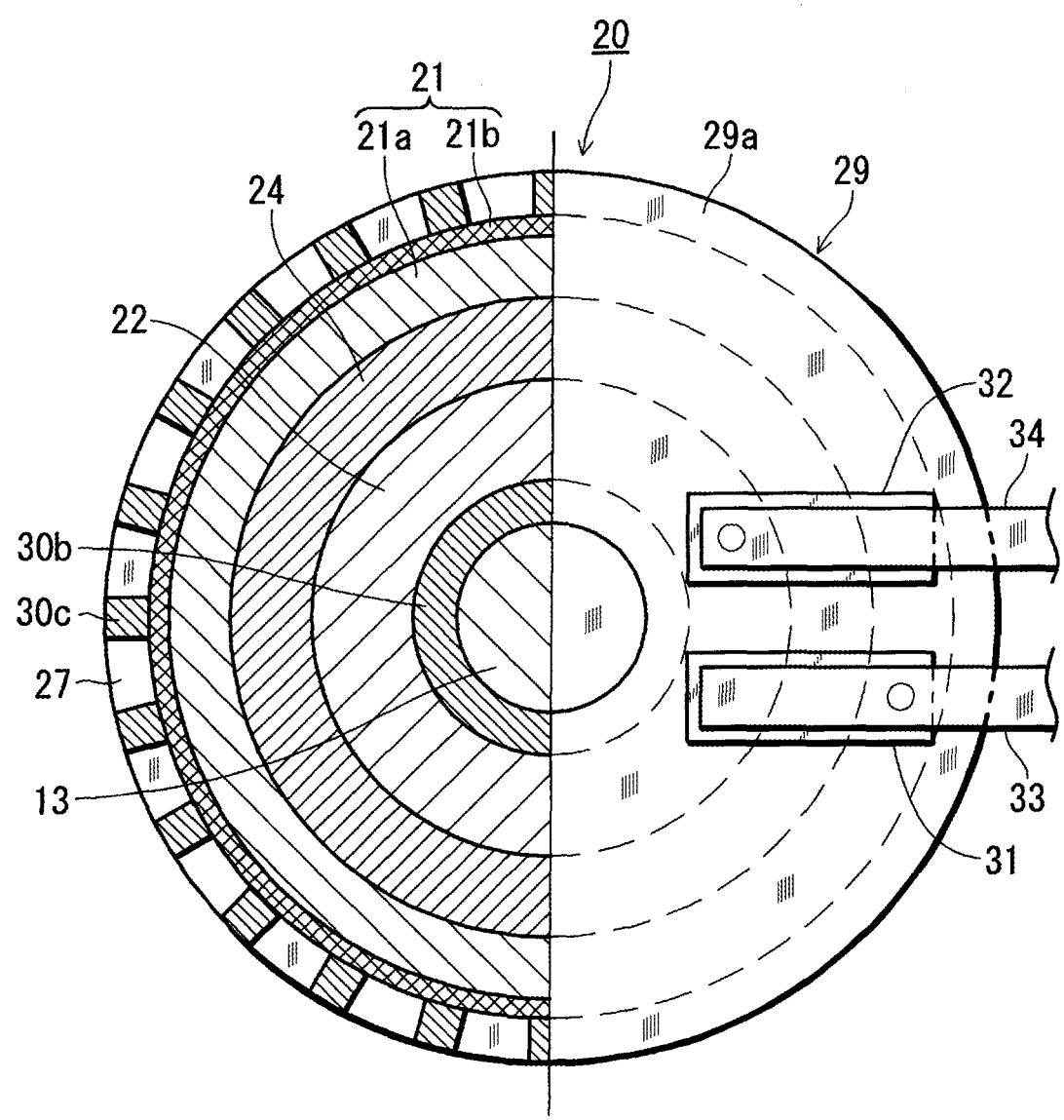
FIG. 3 is a side semi-sectional view of the magnesium-air battery.

FIG. 2 is a side sectional view of the magnesium-air battery 20, and FIG. 3 is a side semi-sectional view of the magnesium-air battery 20. As described above, the magnesium-air battery 20 has the anode 21, the cathode 22, the liquid holder 23, and the liquid absorber 24. The cathode 22 is made of magnesium or an alloy of magnesium, and placed in one end portion of the magnesium-air battery 20. When liquid exists in the detection point, the liquid absorber 24 is soaked with the liquid, and the liquid is held as an electrolyte solution in the liquid holder 23, whereby the magnesium is caused to elute into the liquid functioning as an electrolyte solution ($2Mg \rightarrow 2Mg^{2+}+4e^-$) to generate magnesium ions.

The liquid holder 23 is usually called a separator, placed between the anode 21 and the cathode 22 to prevent a short circuit from occurring, and has liquid holding and capillary functions of impregnation and holding of the liquid serving as an electrolyte solution. As the liquid holder 23, useful are cloth in which natural fibers, synthetic fibers, glass fibers, or the like are main components, nonwoven cloth, filter pater, or the like. However, the material is not particularly limited to these materials as far as the material is insulative and has liquid holding and capillary functions. This is applicable also to the materials of the above-described liquid sucking wick 13 and a liquid absorber which will be described later.

The electrolyte solution is the liquid the presence of which is to be detected by the liquid presence detecting device functioning also as a power supply according to the invention.

The anode 21 is configured by an oxygen adsorbent 21a and an anode collector 21b.

The oxygen adsorbent 21a is in close contact with the liquid holder 23, and has a porous property. The oxygen adsorbent 21a adsorbs oxygen in the air functioning as the anode. The oxygen adsorbent 21a may have a configuration where an oxygen adsorbing material such as activated carbon is in air gaps of a porous body, or that where the oxygen adsorbent 21a itself is configured by carbon fibers of activated carbon. Examples of a porous body holding an oxygen adsorbing material are nonwoven cloth and the like. When the liquid exists in the detection point, the liquid absorber 24 is soaked with the liquid, and the liquid is held as an electrolyte solution in the liquid holder 23, thereby causing the liquid functioning as an electrolyte solution to seep also into the oxygen adsorbent 21a. At this time, the oxygen adsorbent 21a adsorbs and reduces oxygen in the air functioning as the anode 21, to generate hydroxide ions in the liquid functioning as an electrolyte solution ($O_2+2H_2O+4e^- \rightarrow 4OH^-$).

The anode collector 21b is placed in the other end portion of the magnesium-air battery 20. The anode collector 21b has an air permeable property. The anode collector 21b is formed by an electrically conductive material, connected to the oxygen adsorbent 21a, and supplies electrons to the oxygen adsorbent 21a. As the anode collector 21b, for example, a metal net having an air permeable property, such as a copper net may be used. In the magnesium-air battery 20, in the direction from the one end portion to the other end portion, the cathode 22, the liquid holder 23, the oxygen adsorbent 21a, and the anode collector 21b are stacked in this sequence and closely contacted.

The liquid absorber 24 causes the magnesium-air battery 20 not only to be used as a power supply, but also to function as a liquid sensor sensing section having a self-power generating function to detect the presence of liquid. In short, the magnesium-air battery 20 is configured as a liquid sensor. The liquid absorber 24 extends from the liquid holder 23 to the liquid presence detection point. When the liquid exists in the detection point, the liquid absorber 24 is soaked with the liquid, and the liquid is held as an electrolyte solution in the liquid holder 23, whereby the magnesium-air battery 20 is caused to operate. When the liquid does not exist in the detection point, the liquid holder 23 is kept to a dry state, whereby the magnesium-air battery 20 is caused to stop. The liquid absorber 24 may be made of a material which is identical with or different from that of the liquid holder 23, and disposed separately therefrom, and the one end portion of the liquid absorber 24 may be connected to the liquid holder 23. Alternatively, it is preferable that the liquid absorber may be formed integrally with the liquid holder 23 in view of the flowability of the liquid and the productivity of the magnesium-air battery 20.

The thus configured magnesium-air battery 20 may be formed into an arbitrary shape such as a rectangular shape, a circular shape, a sheet-like shape, a plate-like shape, a box-like shape, a rod-like shape, and a cylindrical shape. Also the rigidity and the flexibility may be arbitrarily set. The magnesium-air battery may be used in every kind of product in addition to an air improving device.

Under a high temperature environment, the self discharge of a dry battery (a manganese battery or an alkaline battery) advances during stoppage, and the capacity is reduced. Since lithium reacts vigorously with water, sufficient attention must be given in disposal of a used lithium battery. In the device, the magnesium-air battery 20 is used. Therefore, the device can be used even under a high temperature environment, and disposed as general refuse.

In the thus configured liquid presence detecting device functioning also as a power supply according to the invention, when the liquid exists in the detection point, the magnesium-air battery 20 operates (generates electricity), and, when the liquid does not exist in the detection point, the operation of the magnesium-air battery 20 stops. Therefore, an electrical difference between a state where liquid exists in the detection point, and that where liquid does not exist can be captured by using the magnesium-air battery 20, and the presence of liquid can be electrically detected. Namely, the liquid presence detecting device functioning also as a power supply according to the invention has a self-power generating function (the magnesium-air battery 20), can electrically detect the presence of the liquid depending on the supply/stop of the self-generated power, has a simple and compact configuration which does not require an external power supply, and is highly efficient. Next, the configuration of the liquid presence detecting device functioning also as a power supply ac-cording to the invention and in the air improving device will be specifically described. In the air improving device, as shown in FIGS. 1 to 3, the magnesium-air battery 20 has a cylindrical shape where the anode 21 is located outside the liquid holder 23, the cathode 22 is located inside the liquid holder 23, and a liquid sucking wick through hole 25 through which the liquid sucking wick 13 can be passed is formed. The liquid sucking wick 13 has a cylindrical shape. The magnesium-air battery 20 is mounted on the cover member 14, and placed around the liquid sucking wick 13 which is upward projected from the cover member 14. The liquid absorber 24 is passed through a liquid absorber through hole 14a which is disposed in the cover member 14 and outside the liquid sucking wick 13, and extends to the detection point in the vessel body 12. The electrical load 40 is mounted on the device body 1, and, when the air improver 10 is attached into the device body 1, electrically connected to the magnesium-air battery 20.

In the air improving device, when the air improving liquid 11 in the vessel body 12 vanishes, the air improvement effect disappears. In the liquid presence detecting device functioning also as a power supply according to the invention, therefore, it is necessary to detect that the remaining amount of the air improving liquid 11 is reduced (roughly speaking, "empty detection"). Consequently, a liquid level LLOW (FIG. 1) at which the remaining amount of the air improving liquid 11 is small, and which is near the bottom surface 12b of the vessel body 12 is set as the detection point where the presence of the air improving liquid 11 is to be detected. The liquid absorber 24 extends in the vessel body 12 so that the lower end 24a of the liquid absorber is located at a level substantially equal to that of the detection point LLOW. The liquid absorber 24 may extend from one place of the lower end portion of the liquid holder 23 in, for example, one linear shape or one band-like shape, or from several places of the lower end portion of the liquid holder 23 in, for example, linear shapes or band-like shapes. The liquid sucking wick through hole 25 is disposed in a position which is opposed to the liquid absorber extending place of the liquid holder 23, and in a substantially same shape as the lateral section shape of the liquid absorber 24. As the electrical load 40, for example, an LED (Light Emitting Diode) for notifying the user that the remaining amount of the air improving liquid 11 is small, an electronic circuit of a control board through which the LED and the magnesium-air battery 20 are electrically connected to each other, and which applies an operation voltage, and the like may be disposed.

In the air improving device, when the air improving liquid 11 exists in the detection point LLOW, the lower end 24a of the liquid absorber 24 is positioned lower than the detection point LLOW. Therefore, the liquid absorber 24 is soaked with the air improving liquid 11, and the air improving liquid 11 seeping into the liquid absorber 24 is sucked up to the upper portion of the liquid absorber 24 by means of the capillary action. Moreover, the air improving liquid 11 which is sucked up to the upper portion of the liquid absorber 24 is further sucked by the liquid holder 23 into the liquid holder itself by means of the capillary action, and the air improving liquid 11 is held as an electrolyte solution in the liquid holder 23. As a result, the magnesium-air battery 20 operates (generates electricity), and, for example, the electronic circuit of the control board applies the operation voltage to the LED to turn on the LED. By contrast, when the remaining amount of the air improving liquid 11 becomes small, and the level of the air improving liquid 11 is lower than the detection point LLOW, the lower end 24a of the liquid absorber 24 is exposed to the air, and therefore the air improving liquid 11 held in the liquid absorber 24 and the liquid holder 23 is returned into the vessel body 12, so that the liquid holder 23 is in a dry state. As a result, the magnesium-air battery 20 stops to operate, and the LED is turned off. The turning on of the LED indicates that the air improvement effect is continued. The turning off of the LED indicates the situation where the air improver 10 is to be replaced with a fresh one.

The thus configured air improving device includes the liquid presence detecting device functioning also as a power supply according to the invention, and the liquid presence detecting device does not require an external power supply. Therefore, the air improving device has a configuration which is correspondingly simplified and compactified, and is a highly efficient device.

In the case where the magnesium-air battery 20 is mounted in the vessel body 12, the magnesium-air battery 20 must be set in the vessel body 12 independently and separately from the liquid sucking wick 13. In the air improving device, by contrast, the magnesium-air battery 20 is mounted on the cover member 14. When the opening 12a of the vessel body 12 is closed by the cover member 14 and the liquid sucking wick 13 is set into the vessel body 12, therefore, also the magnesium-air battery 20 is automatically set into the vessel body 12, and, even when the air improving device includes the liquid presence detecting device, the air improver 10 can be easily assembled. In the air improving device, although the electrical load 40 is mounted on the device body 1, the load is electrically connected to the magnesium-air battery 20 when the air improver 10 is attached into the device body 1. When the air improving device is assembled into the use state by attaching the air improver 10 into the device body 1, therefore, also the liquid presence detecting device is automatically configured, and, even when the air improving device includes the liquid presence detecting device, the air improving device can be easily assembled into the use state. In the case where the magnesium-air battery 20 is mounted into the vessel body 12, in order to cause the liquid absorber 24 to extend to the detection point LLOW in the vessel body 12, the liquid absorber through hole 14a must be disposed in the vessel body 12 in addition to the opening 12a in the upper portion, and, even when a countermeasure against leaking from the liquid absorber through hole 14a is taken, there is a possibility that leakage may occur during the use. In the air improving device, by contrast, the magnesium-air battery 20 is mounted on the cover member 14, and the liquid absorber 24 is passed through the liquid absorber through hole 14a which is disposed in the cover member 14 and outside the liquid sucking wick 13, and extends to the detection point LLOW in the vessel body 12. Therefore, it is not necessary to dispose the liquid absorber through hole 14a in the vessel body 12 in addition to the opening 12a in the upper portion, and to take a countermeasure against leaking from the liquid absorber through hole 14a, and it is possible to eliminate leakage during the use. Moreover, the magnesium-air battery 20 is mounted on the cover member 14 which is to be attached to the opening 12a of the upper portion of the vessel body 12. Therefore, the level difference between the detection point LLow and the magnesium-air battery 20 is ensured, and, when the air improving liquid 11 is depleted from the state the air improving liquid exists in the detection point LLow, extraction of the air improving liquid 11 from the liquid holder 23, and drying of the liquid holder 23 can be performed for a short time period. Consequently, the responsiveness of the liquid presence detecting device can be improved.

Figure 4:
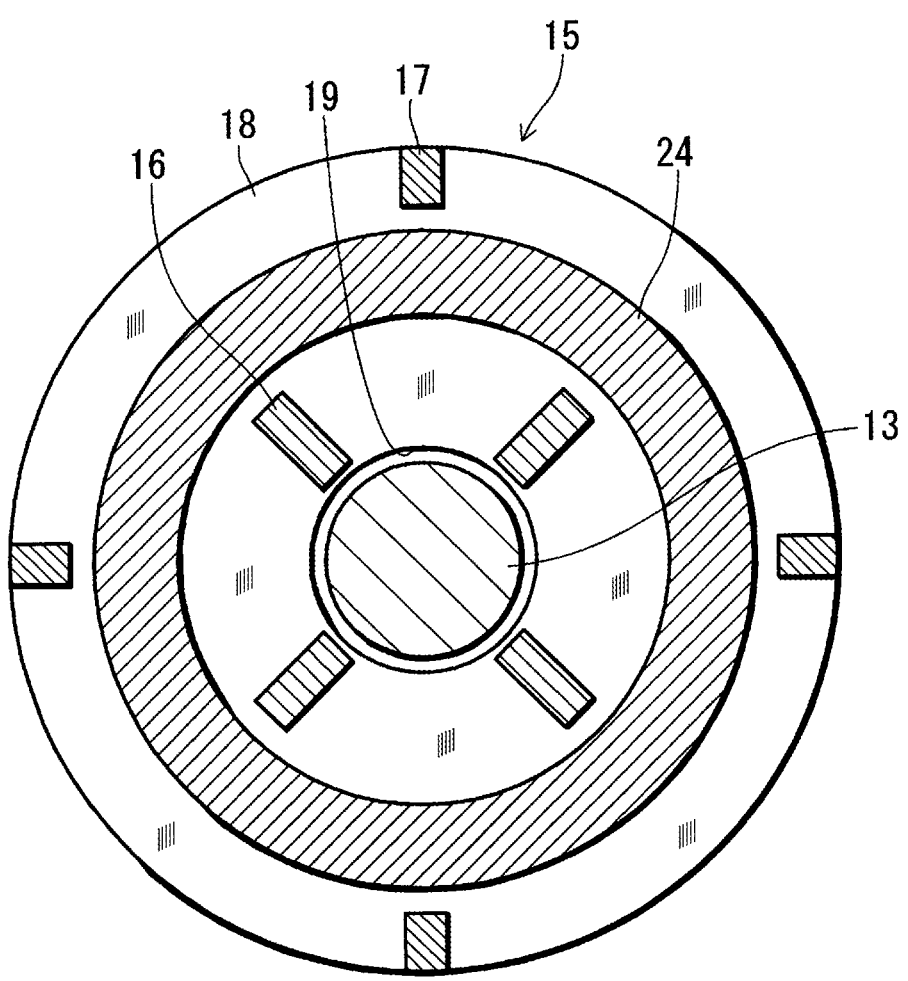
FIG. 4 is a plan sectional view showing a wick portion of a cover member.

In the air improving device, the liquid absorber 24 has a cylindrical shape, the liquid absorber through hole 14a has an annular shape, and a wick portion 15 which is to be inserted from the opening 12a into the vessel body 12 is formed integrally with the cover member 14. FIG. 4 is a plan sectional view showing the wick portion 15 of the cover member 14. As shown in FIGS. 1 and 4, the wick portion 15 is configured by: a plurality of inner vertical bar portions 16 which downward extend from the lower surface of the cover member 14 and inside the liquid absorber through hole 14a, and which are placed at predetermined intervals along the circumferential direction of the liquid absorber through hole 14a; a plurality of outer vertical bar portions 17 which downward extend from the lower surface of the cover member 14 and outside the liquid absorber through hole 14a, and which are placed at predetermined intervals along the circumferential direction of the liquid absorber through hole 14a; and a coupling portion 18 which couples together the lower ends of the inner vertical bar portions 16 and the outer vertical bar portions 17. The portions of the cover member 14 which are respectively inside and outside the liquid absorber through hole 14a, and which are separated from each other by the annular liquid absorber through hole 14a are integrated with each other to provide the cover member 14 with an integral structure. The cylindrical liquid absorber 24 is received between the inner vertical bar portions 16 and the outer vertical bar portions 17 from the annular liquid absorber through hole 14a, and placed around the liquid sucking wick 13.

In the thus configured air improving device, in both the cases where the device in the use is placed on a horizontal plane, and where the device in the use is placed on an inclined plane, the effective air improving liquid 11 which is actually used in diffusion is the air improving liquid 11 which is in contact with the liquid sucking wick 13. Since the cylindrical liquid absorber 24 is placed around the liquid sucking wick 13, it is possible to always detect the presence of the effective air improving liquid 11, and the accuracy of the liquid presence detecting device can be improved. Moreover, the liquid absorber of the magnesium-air battery 20 can extend downward straightly from the liquid holder 23 to the effective detection point LLOW, and the sucking and holding of the air improving liquid 11 into the liquid holder 23, and the withdrawal of the air improving liquid 11 from the liquid holder 23 can be performed for a short time period. Therefore, the responsiveness of the liquid presence detecting device can be improved.

In the air improving device, a lower liquid sucking wick through hole 19 through which the liquid sucking wick 13 can be passed is disposed in a central portion of the coupling portion 18, the coupling portion 18 is placed in a height position which is separated from the bottom surface 12b of the vessel body 12, the liquid sucking wick 13 is passed through the lower liquid sucking wick through hole 19 to be in contact with the bottom surface 12b of the vessel body 12, and the lower end 24a of the liquid absorber 24 butts against the coupling portion 18.

In the thus configured air improving device, the liquid sucking wick 13 is passed through the lower liquid sucking wick through hole 19 to be in contact with the bottom surface 12b of the vessel body 12, and the lower end 24a of the liquid absorber 24 butts against the coupling portion 18. Even when the device is handled in a somewhat rough manner during the use, therefore, the liquid sucking wick 13 and the cover member 14 can be prevented from being bent or positionally displaced, and therefore the air improvement performance and the liquid detection performance can be maintained.

In the air improving device, an electrode case 28 which has a liquid absorber extraction port 26 and air intake ports 27 for the anode 21, which houses the anode 21, the cathode 22, and the liquid holder 23, and which is made of an insulating synthetic resin is disposed in the magnesium-air battery 20. The electrode case 28 is configured by an upper case 29 and a lower case 30. In the upper case 29, an electrode case top wall portion 29a, an electrode case upper inner wall portion 29b, and an electrode case upper outer wall portion 29c are integrally formed. The electrode case top wall portion 29a has annular shape, and covers the upper surfaces of the anode 21, the cathode 22, and the liquid holder 23. The electrode case upper inner wall portion 29b has a cylindrical shape which downward extends from an inner peripheral edge of the electrode case top wall portion 29a along the inner circumferential surface of the cathode 22, and which covers an upper portion of the inner circumferential surface of the cathode 22. The electrode case upper outer wall portion 29c has a cylindrical shape which downward extends from an outer peripheral edge of the electrode case top wall portion 29a along the outer circumferential surface of the anode 21, and which covers an upper portion of the outer circumferential surface of the anode 21. In the lower case 30, an electrode case bottom wall portion 30a, an electrode case lower inner wall portion 30b, and an electrode case lower outer wall portion 30c are formed integrally with the cover member 14. The electrode case bottom wall portion 30a is configured by a part of the cover member 14 opposed to the lower surfaces of the anode 21 and the cathode 22, covers the lower surfaces of the anode 21 and the cathode 22, and has the liquid absorber through hole 14a as the liquid absorber extraction port 26. The electrode case lower inner wall portion 30b has a cylindrical shape which rises from an inner peripheral edge of the electrode case bottom wall portion 30a along the inner circumferential surface of the cathode 22, and covers a lower portion of the inner circumferential surface of the cathode 22. The electrode case lower outer wall portion 30c has a cylindrical shape which rises from an outer peripheral edge of the electrode case bottom wall portion 30a along the outer circumferential surface of the anode 21, and covers a lower portion of the outer circumferential surface of the anode 21. The upper case 29 and the lower case 30 are integrated with each other in a state where the lower end of the electrode case upper inner wall portion 29b, and the upper end of the electrode case lower inner wall portion 30b are butted against each other, and the lower end of the electrode case upper outer wall portion 29c, and the upper end of the electrode case lower outer wall portion 30c are butted against each other. The electrode case 28 passingly holds the liquid sucking wick 13 inside the electrode case upper inner wall portion 29b and the electrode case lower inner wall portion 30b, and the plurality of air intake ports 27 are disposed at the predetermined intervals in the circumferential direction while extending over one or both of the electrode case upper outer wall portion 29c and the electrode case lower outer wall portion 30c.

In the thus configured air improving device, the liquid sucking wick 13, the cover member 14, and the magnesium-air battery 20 are integrated with one another by using the electrode case 28 of the magnesium-air battery 20, and these components can be handled as one component in the assembling of the air improver 10 during the use. Therefore, the assemblability during the use can be improved while suppressing the production cost.

In the air improving device, moreover, an anode terminal 31 which is fixed in a state where one end side is in contact with the anode collector 21b of the anode 21, and in a state where the other end side is exposed from the upper surface of the upper case 29, and a cathode terminal 32 which is fixed in a state where one end side is in contact with the cathode 22, and in a state where the other end side is exposed from the upper surface of the upper case 29 are disposed in the upper case 29. An anode connection terminal 33 which, when the air improver 10 is attached into the device body 1, is elastically contacted with the anode terminal 31, a cathode connection terminal 34 which is elastically contacted with the cathode terminal 32, and a control board 35 to which the anode connection terminal 33, the cathode connection terminal, and the electrical load 40 are electrically connected are disposed in the device body 1.

Here, the anode connection terminal 33, the cathode connection terminal, and the electrical load 40 may be directly soldered (mounted) to the control board 35 to be electrically connected thereto, or may be fixed to the device housing 2 and electrically connected to the control board through lead wires or the like.

In the thus configured air improving device, when the air improver 10 is attached into the device body 1, the anode terminal 31 and the anode connection terminal 33, and the cathode terminal 32 and the cathode connection terminal 34 are electrically connected to each other. When the air improving device is assembled into the use state by attaching the air improver 10 into the device body 1, therefore, also the liquid presence detecting device is automatically configured, and, even when the air improving device includes the liquid presence detecting device, the air improving device can be easily assembled into the use state.

Embodiment 2

Figure 5:
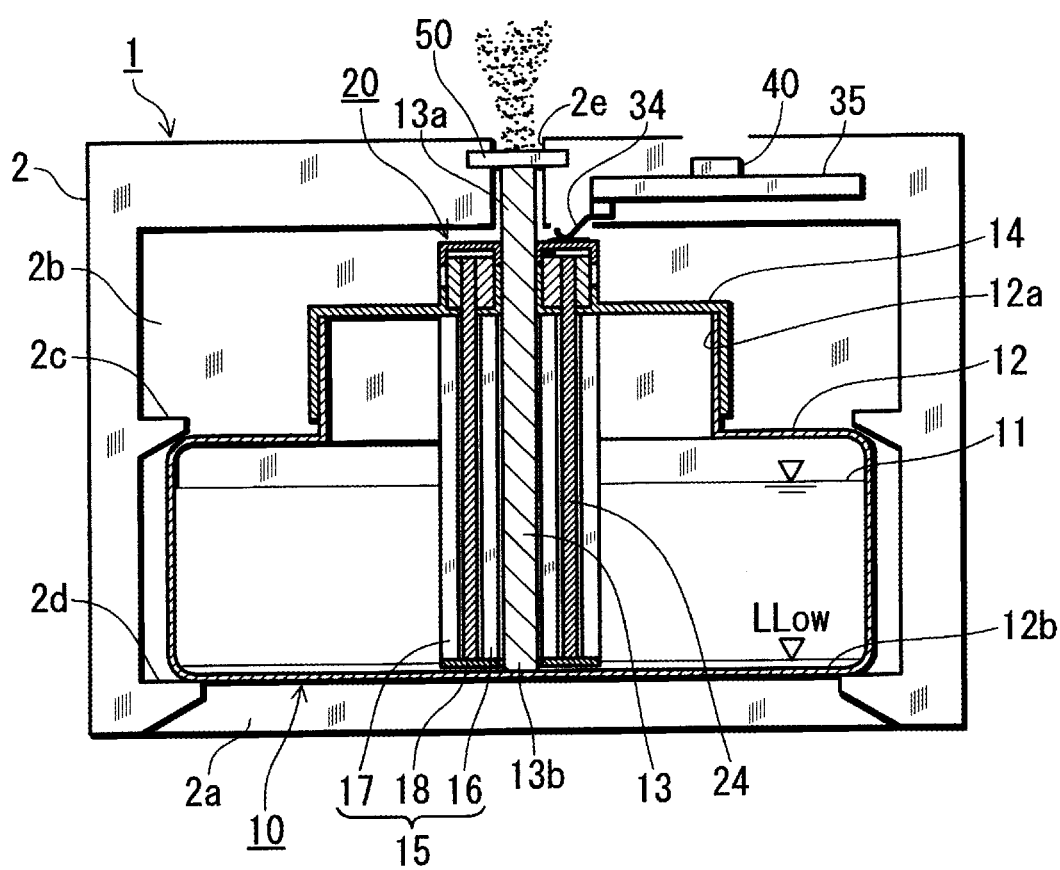
FIG. 5 is an overall configuration diagram of an air improving device which shows Embodiment 2 of the liquid presence detecting device functioning also as a power supply according to the invention.

FIG. 5 is an overall configuration diagram of an air improving device which shows Embodiment 2. The components which are identical with those of the air improving device of Embodiment 1 are denoted by the same reference numerals.

The air improving device of the embodiment includes a spray unit 50. The spray unit 50 is attached to the diffusion port 2e of the device housing 2. In the spray unit 50, a metal plate having a plurality of nozzle holes is vibrated, the air improving liquid 11 which is supplied from the liquid sucking wick 13 to the rear surface side (lower surface side) of the metal plate, i.e., the diaphragm is sprayed through the plurality of nozzle holes to the front surface side of the diaphragm, and the air improving component is diffused into the room from the diffusion port 2e of the device housing 2.

The air improving device of the embodiment includes the liquid presence detecting device functioning also as a power supply according to the invention, and is configured so that the spray unit 50 is electrically connected to the control board 35 to function as one of electrical loads which consume power generated by the magnesium-air battery 20, the liquid absorber 24 is soaked with the air improving liquid 11 when the air improving liquid 11 exists in the detection point LLow, the air improving liquid 11 is held as an electrolyte solution in the liquid holder 23, whereby the magnesium-air battery 20 is caused to operate, and the spray unit 50 is caused to operate, and, when the air improving liquid 11 does not exist in the detection point LLow, the liquid holder 23 is kept to a dry state, and the magnesium-air battery 20 is caused to stop, whereby the spray unit 50 is automatically stopped. The embodiment can achieve effects of energy saving and preventing "operation with no liquid" from occurring.

Some of air improving devices include an electrical load such as a heater, a fan motor, and a plus or minus ion generation unit. Similarly with the spray unit 50, also such air improving device can be operated and automatically stopped by the liquid detection system in the invention.

Embodiment 3

In the liquid presence detecting device functioning also as a power supply according to the invention which is used in the air improving devices of Embodiments 1 and 2, no presence of the air improving liquid 11 in the vessel body 12 is detected. Among air improving devices, there are devices which must detect a state where a vessel is filled with liquid. In a dehumidifier, for example, dehumidifying liquid is stored in a vessel, and a state where the vessel is filled with the dehumidifying liquid is detected in order to prevent the dehumidifying liquid from overflowing from the vessel. In this case, the dehumidifier is provided with the liquid detection system in the invention, an electrical load (an LED or a buzzer) which consumes power generated by the magnesium-air battery is stopped until the state where the vessel is filled with the liquid is detected, and, when the state is detected, the electrical load can be automatically operated.

Next, several other use example of the liquid presence detecting device functioning also as a power supply according to the invention will be described with reference to FIGS. 6 to 10.

Figure 6:
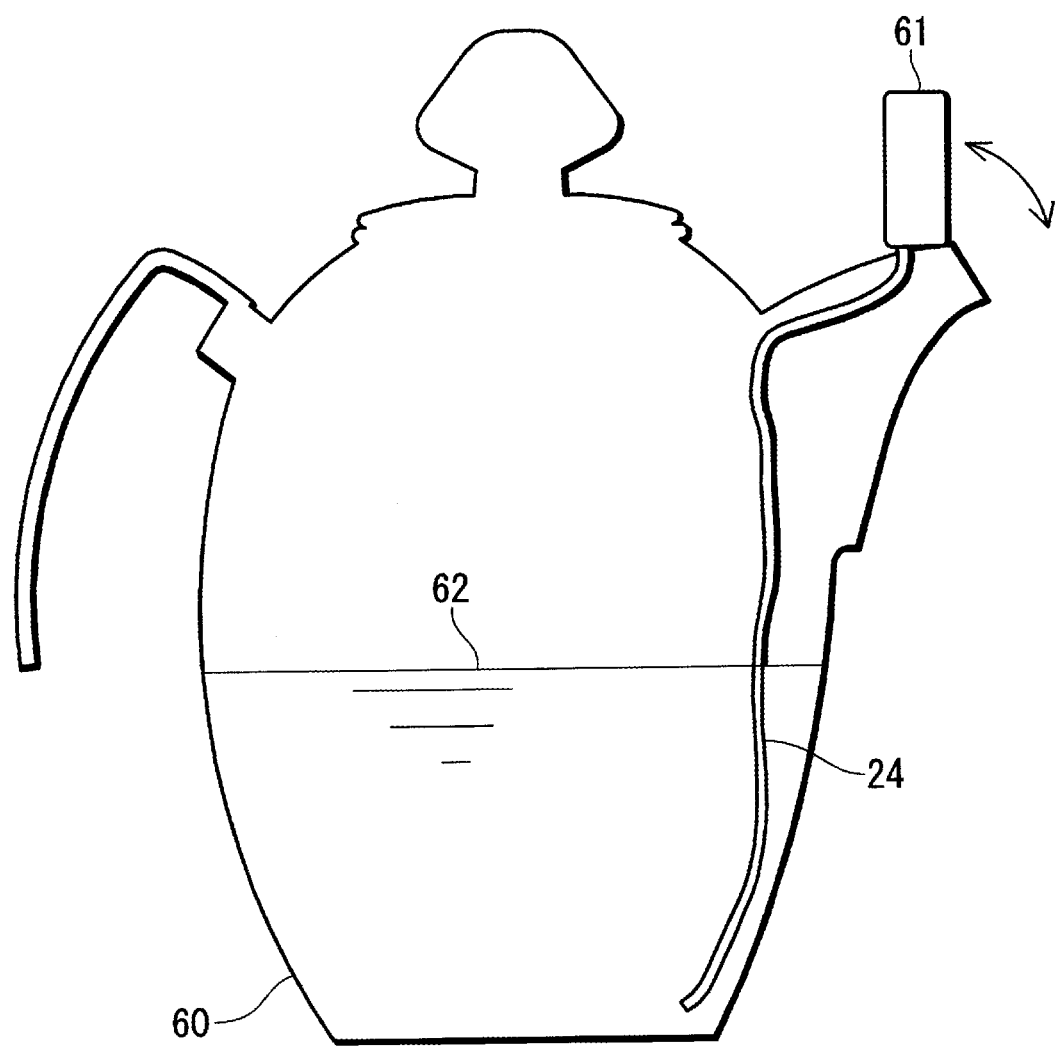
FIG. 6 is a diagram of a kettle which is a use example of the liquid presence detecting device functioning also as a power supply according to the invention.

FIG. 6 is a diagram of a kettle 60 including the liquid presence detecting device functioning also as a power supply according to the invention. For example, an opening/closing lid 61 having a rotary solenoid is disposed in the spout of the kettle 60. In the liquid presence detecting device, the liquid absorber 24 of the magnesium-air battery 20 extends into the kettle 60 (the detection point), and the presence of liquid (tea or the like) 62 in the kettle 60 is detected. When tea exists in the kettle 60, for example, the opening/closing lid 61 is opened, and, when tea does not exist, the spout is closed. According to the configuration, it is possible to know whether tea 62 exists in the kettle 60 or not, without touching the kettle 60.

Figure 7:
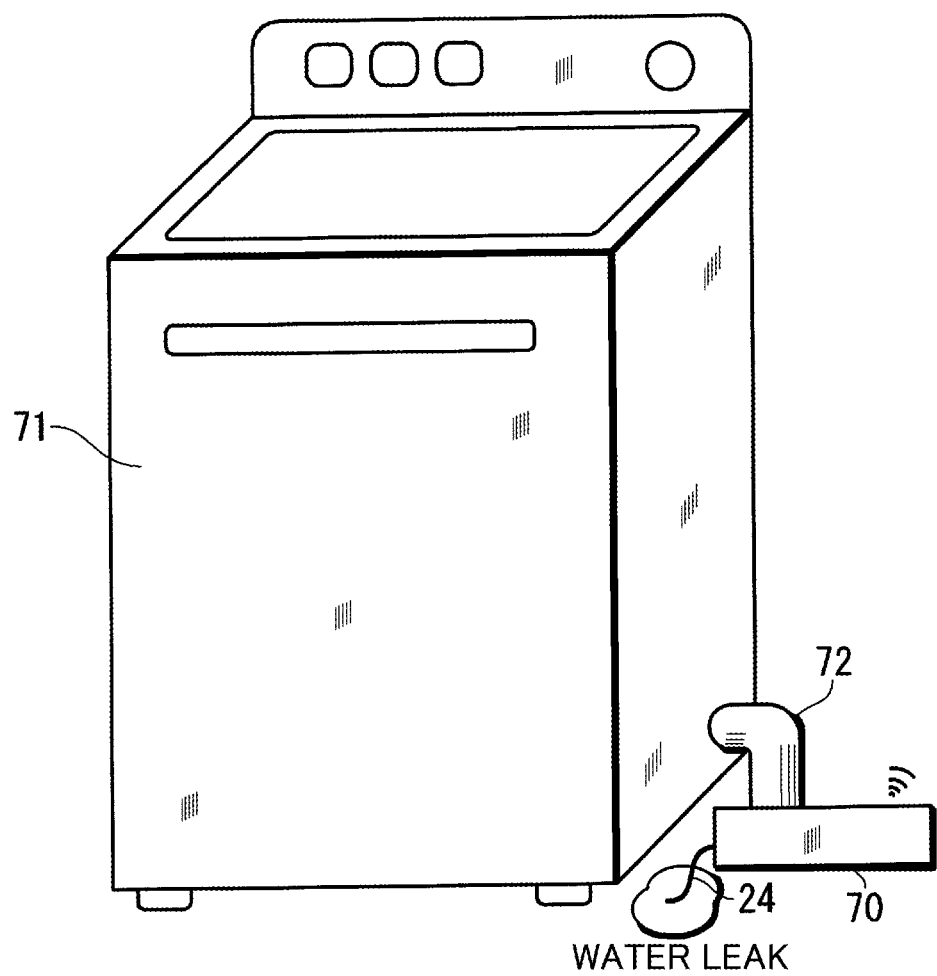
FIG. 7 is a diagram of a water leak sensor which is a use example of the liquid presence detecting device functioning also as a power supply according to the invention.

FIG. 7 is a diagram of a water leak sensor 70 including the liquid presence detecting device functioning also as a power supply according to the invention. For example, the water leak sensor 70 is placed in the vicinity of a drain tube 72 of a washing machine 71. In the liquid presence detecting device, the liquid absorber 24 of the magnesium-air battery 20 extends onto the floor in the vicinity of the drain tube 72 of the washing machine 71, and, when the drain tube 72 is broken and water leak occurs, an alarm is issued by sounding a buzzer. According to the configuration, it is possible to prevent the floor from being flooded.

Figure 8:
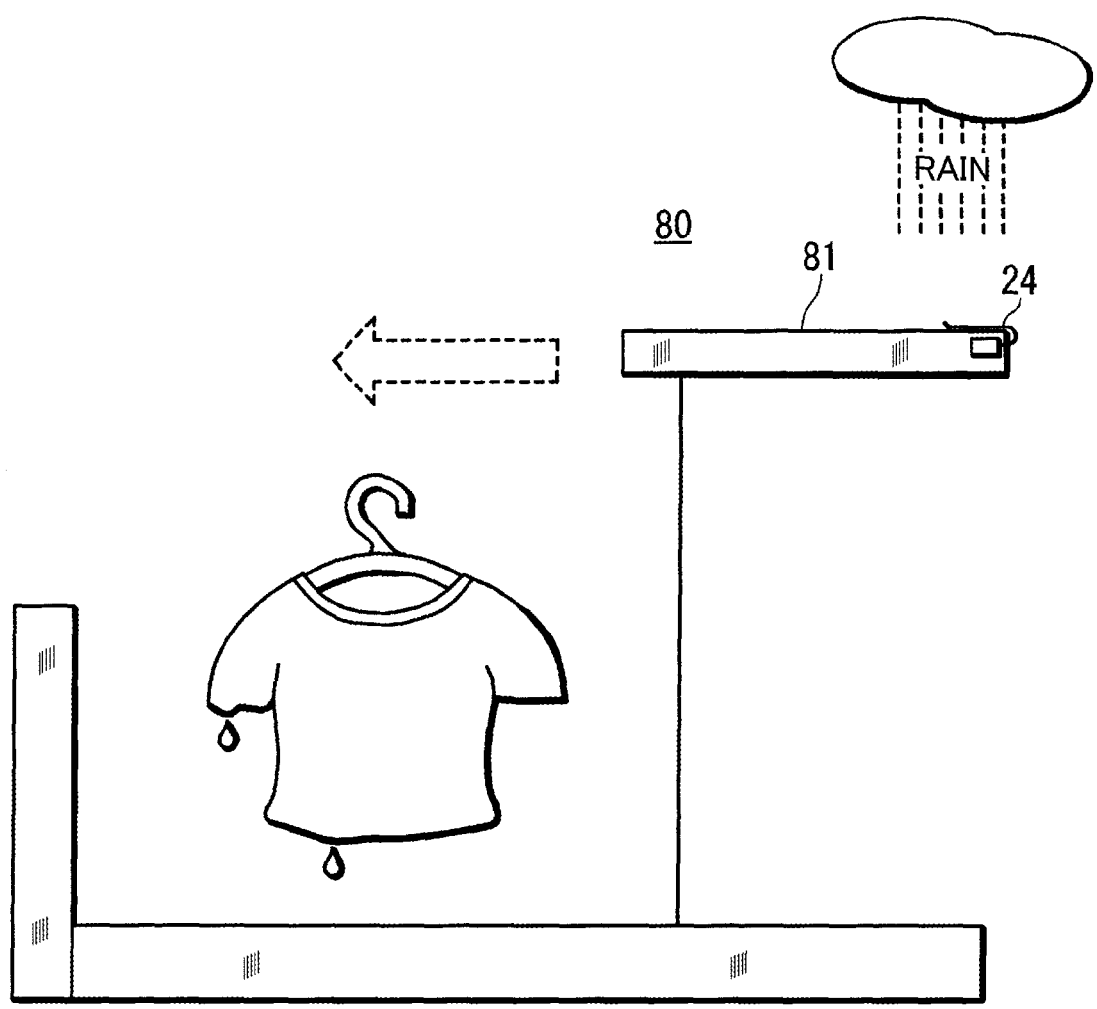
FIG. 8 is a diagram of a rain-preventing apparatus which is a use example of the liquid presence detecting device functioning also as a power supply according to the invention.

FIG. 8 is a diagram of a rain-preventing apparatus 80 including the liquid presence detecting device functioning also as a power supply according to the invention. The rain-preventing apparatus 80 includes a movable roof 81 which is driven by an electric motor. In the liquid presence detecting device, the liquid absorber 24 of the magnesium-air battery 20 extends onto the upper surface of the movable roof 81. When it rains, the movable roof 81 is automatically moved above a drying area to make it possible to prevent the laundry from wetted by rain. The device is effective as a countermeasure against a sudden change of the weather when going out.

Figure 9:
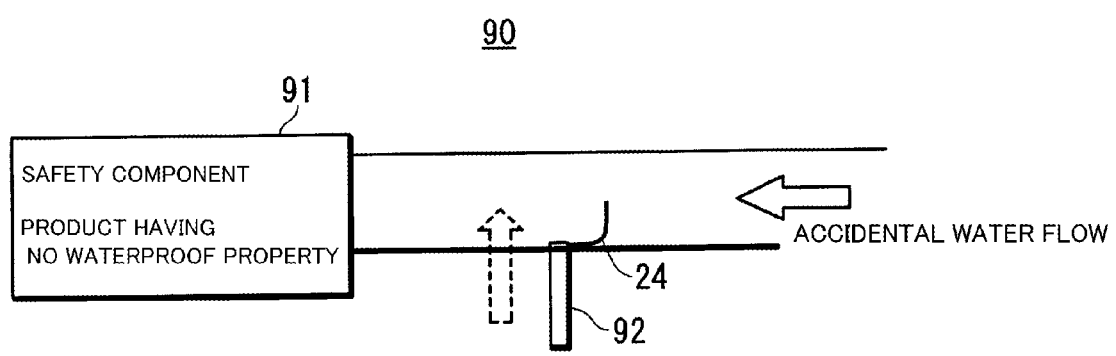
FIG. 9 is a diagram of a water stopping apparatus which is a use example of the liquid presence detecting device functioning also as a power supply according to the invention.

FIG. 9 is a diagram of a water stopping apparatus 90 including the liquid presence detecting device functioning also as a power supply according to the invention. The water stopping apparatus 90 includes a solenoid-driven water stopping shutter 92 for a safety component 91. In the liquid presence detecting device, the liquid absorber 24 of the magnesium-air battery 20 extends to the detection point, and, when water accidentally flows to the safety component, the water stopping shutter 92 is closed. This can prevent the safety component 91 from being damaged by water.

Figure 10:
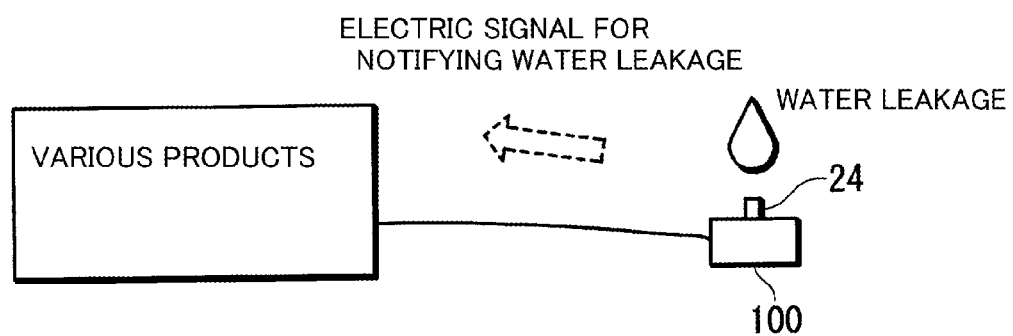
FIG. 10 is a diagram of a long-life water leak sensor which is a use example of the liquid presence detecting device functioning also as a power supply according to the invention.

FIG. 10 is a diagram of a long-life water leak sensor 100 including the liquid presence detecting device functioning also as a power supply according to the invention. The long-life water leak sensor 100 is used as a module which notifies occurrence of water leakage. In the liquid presence detecting device, the liquid absorber 24 of the magnesium-air battery 20 extends to the outside of the module. When water leakage is contacted with the liquid absorber, the device functions as a power supply for driving something, and generates and transmits an electric signal indicating that water leakage occurs in something. When the liquid absorber is not soaked with water, the reaction itself is not caused. Therefore, replacement of the device is not necessary for a long term.

The liquid presence detecting device functioning also as a power supply according to the invention can be used in various fields in addition to the above-described use examples. For example, the device can be used in an electric float for fishing, lantern for a ceremony of floating lanterns, water illumination, rescue transmitter for heavy rain disaster, or the like which, when seawater or freshwater is detected, is lit on by the self-generated power. Moreover, the device can be used in a disposal diaper or the like, and, when urination or defecation is detected, is caused to communicate with a management center such as a hospital or a nursing home by the self-generated power.

DESCRIPTION OF REFERENCE NUMERALS 1 device body
10 air improver
11 air improving liquid
12 vessel body
12a opening
13 liquid sucking wick
14 cover member
14a liquid absorber through hole
15 wick portion
16 inner vertical bar portion
17 outer vertical bar portion
18 coupling portion
19 lower liquid sucking wick through hole
20 magnesium-air battery
21 anode
22 cathode
23 liquid holder
24 liquid absorber
25 liquid sucking wick through hole
26 liquid absorber extraction port
27 air intake port
28 electrode case
29 upper case
29a electrode case top wall portion
29b electrode case upper inner wall portion
29c electrode case upper outer wall portion
30 lower case
30a electrode case bottom wall portion
30b electrode case lower inner wall portion
30c electrode case lower outer wall portion
31 anode terminal
32 cathode terminal
33 anode connection terminal
34 cathode connection terminal
35 control board
40 electrical load
L Low detection point

The invention claimed is:

1. A liquid presence detecting device functioning also as a power supply, said device including a magnesium-air battery and an electrical load that consumes power generated by the magnesium-air battery, wherein the magnesium-air battery comprises an anode, a cathode, a liquid holder that is placed between the anode and cathode, and a liquid absorber that extends from the liquid holder to a detection point where a presence of a liquid is to be detected, and, when the liquid exists at the detection point, the liquid absorber is soaked with the liquid, and the liquid is held as an electrolyte solution in the liquid holder, whereby the magnesium-air battery is caused to operate.

2. The liquid presence detecting device functioning also as a power supply according to claim 1, wherein the liquid is stored in a vessel, and a presence of the liquid stored in the vessel is detected.

3. An air improving device wherein the device includes the liquid presence detecting device functioning also as a power supply according to claim 1, a device body, and an air improver which is detachably attached into the device body,
the air improver has: air improving liquid; a vessel body which has an opening in an upper portion, and which stores the air improving liquid; a liquid sucking wick which is inserted into the vessel body from the opening, and which is impregnated with the air improving liquid to suck up the liquid by means of a capillary action; and a detachable cover member which passingly holds the liquid sucking wick in a central portion, which, when the cover member is attached to the opening of the vessel body to close the opening, insertingly holds the liquid sucking wick into the vessel body, and which is made of an insulating material,
the magnesium-air battery has a cylindrical shape in which the anode is located outside the liquid holder, the cathode is located inside the liquid holder, and a liquid sucking wick through hole through which the liquid sucking wick is passable is formed,
the magnesium-air battery is mounted on the cover member, and placed around the liquid sucking wick which is upward projected from the cover member, the liquid absorber is passed through a liquid absorber through hole which is disposed in the cover member and outside the liquid sucking wick, and extends to the detection point in the vessel body, and
the electrical load is mounted on the device body, and, when the air improver is attached into the device body, electrically connected to the magnesium-air battery.

4. The air improving device according to claim 3, wherein the liquid absorber has a cylindrical shape,
the liquid absorber through hole has an annular shape,
a wick portion which is to be inserted from the opening into the vessel body is formed integrally with the cover member,
the wick portion is configured by: a plurality of inner vertical bar portions which downward extend from a lower surface of the cover member and inside the liquid absorber through hole, and which are placed at predetermined intervals along a circumferential direction of the liquid absorber through hole; a plurality of outer vertical bar portions which downward extend from the lower surface of the cover member and outside the liquid absorber through hole, and which are placed at predetermined intervals along the circumferential direction of the liquid absorber through hole; and a coupling portion which couples together lower ends of the inner vertical bar portions and the outer vertical bar portions,
portions of the cover member which are respectively inside and outside the liquid absorber through hole, and which are separated from each other by the annular liquid absorber through hole are integrated with each other to provide the cover member with an integral structure, and
the cylindrical liquid absorber is received between the inner vertical bar portions and the outer vertical bar portions from the annular liquid absorber through hole, and placed around the liquid sucking wick.

5. The air improving device according to claim 4, wherein a lower liquid sucking wick through hole through which the liquid sucking wick is passable is disposed in a central portion of the coupling portion, the coupling portion is placed in a height position which is separated from the bottom surface of the vessel body, the liquid sucking wick is passed through the lower liquid sucking wick through hole to be in contact with the bottom surface of the vessel body, and a lower end of the liquid absorber butts against the coupling portion.

6. The air improving device according to claim 5, wherein
an electrode case which has a liquid absorber extraction port and air intake ports for the anode, which houses the anode, the cathode, and the liquid holder, and which is made of an insulating material is disposed in the magnesium-air battery,
the electrode case is configured by an upper case and a lower case,
an electrode case top wall portion, an electrode case upper inner wall portion, and an electrode case upper outer wall portion are integrally formed in the upper case,
the electrode case top wall portion has annular shape, and covers upper surfaces of the anode, the cathode, and the liquid holder,
the electrode case upper inner wall portion has a cylindrical shape which downward extends from an inner peripheral edge of the electrode case top wall portion along an inner circumferential surface of the cathode, and which covers an upper portion of the inner circumferential surface of the cathode,
the electrode case upper outer wall portion has a cylindrical shape which downward extends from an outer peripheral edge of the electrode case top wall portion along the outer circumferential surface of the anode, and which covers an upper portion of the outer circumferential surface of the anode,
in the lower case, an electrode case bottom wall portion, an electrode case lower inner wall portion, and an electrode case lower outer wall portion are formed integrally with the cover member,
the electrode case bottom wall portion is configured by a part of the cover member opposed to the lower surfaces of the anode and the cathode, covers the lower surfaces of the anode and the cathode, and has the liquid absorber through hole as the liquid absorber extraction port,
the electrode case lower inner wall portion has a cylindrical shape which rises from an inner peripheral edge of the electrode case bottom wall portion along the inner circumferential surface of the cathode, and covers a lower portion of the inner circumferential surface of the cathode,
the electrode case lower outer wall portion has a cylindrical shape which rises from an outer peripheral edge of the electrode case bottom wall portion along the outer circumferential surface of the anode, and covers an lower portion of the outer circumferential surface of the anode,
the upper case and the lower case are integrated with each other in a state where the lower end of the electrode case upper inner wall portion, and the upper end of the electrode case lower inner wall portion are butted against each other, and the lower end of the electrode case upper outer wall portion, and the upper end of the electrode case lower outer wall portion are butted against each other,
the electrode case passingly holds the liquid sucking wick inside the electrode case upper inner wall portion and the electrode case lower inner wall portion, and
the plural air intake ports are disposed at predetermined intervals in the circumferential direction while extending over one or both of the electrode case upper outer wall portion and the electrode case lower outer wall portion.

7. The air improving device according to claim 6, wherein an anode terminal which is fixed in a state where one end side is in contact with the anode, and in a state where another end side is exposed from the upper surface of the upper case, and a cathode terminal which is fixed in a state where one end side is in contact with the cathode, and in a state where another end side is exposed from the upper surface of the upper case are disposed in the upper case, and an anode connection terminal which, when the air improver is mounted into the device body, is elastically contacted with the anode terminal, a cathode connection terminal which, when the air improver is mounted into the device body, is elastically contacted with the cathode terminal, and a control board to which the anode connection terminal, the cathode connection terminal, and the electrical load are electrically connected are disposed in the device body.

8. An air improving device wherein the device includes the liquid presence detecting device functioning also as a power supply according to claim 2, a device body, and an air improver which is detachably attached into the device body,
the air improver has: air improving liquid; a vessel body which has an opening in an upper portion, and which stores the air improving liquid; a liquid sucking wick which is inserted into the vessel body from the opening, and which is impregnated with the air improving liquid to suck up the liquid by means of a capillary action; and a detachable cover member which passingly holds the liquid sucking wick in a central portion, which, when the cover member is attached to the opening of the vessel body to close the opening, insertingly holds the liquid sucking wick into the vessel body, and which is made of an insulating material,
the magnesium-air battery has a cylindrical shape in which the anode is located inside the liquid holder, the cathode is located outside the liquid holder, and a liquid sucking wick through hole through which the liquid sucking wick is passable is formed,
the magnesium-air battery is mounted on the cover member, and placed around the liquid sucking wick which is upward projected from the cover member, the liquid absorber is passed through a liquid absorber through hole which is disposed in the cover member and outside the liquid sucking wick, and extends to the detection point in the vessel body, and
the electrical load is mounted on the device body, and, when the air improver is attached into the device body, electrically connected to the magnesium-air battery.

9. The air improving device according to claim 8, wherein the liquid absorber has a cylindrical shape,
the liquid absorber through hole has an annular shape,
a wick portion which is to be inserted from the opening into the vessel body is formed integrally with the cover member,
the wick portion is configured by: a plurality of inner vertical bar portions which downward extend from a lower surface of the cover member and inside the liquid absorber through hole, and which are placed at predetermined intervals along a circumferential direction of the liquid absorber through hole; a plurality of outer vertical bar portions which downward extend from the lower surface of the cover member and outside the liquid absorber through hole, and which are placed at predetermined intervals along the circumferential direction of the liquid absorber through hole; and a coupling portion which couples together lower ends of the inner vertical bar portions and the outer vertical bar portions, portions of the cover member which are respectively inside and outside the liquid absorber through hole, and which are separated from each other by the annular liquid absorber through hole are integrated with each other to provide the cover member with an integral structure, and the cylindrical liquid absorber is received between the inner vertical bar portions and the outer vertical bar portions from the annular liquid absorber through hole, and placed around the liquid sucking wick.

10. The air improving device according to claim 9, wherein a lower liquid sucking wick through hole through which the liquid sucking wick is passable is disposed in a central portion of the coupling portion, the coupling portion is placed in a height position which is separated from the bottom surface of the vessel body, the liquid sucking wick is passed through the lower liquid sucking wick through hole to be in contact with the bottom surface of the vessel body, and a lower end of the liquid absorber butts against the coupling portion.

11. The air improving device according to claim 10, wherein
an electrode case which has a liquid absorber extraction port and air intake ports for the anode, which houses the anode, the cathode, and the liquid holder, and which is made of an insulating material is disposed in the magnesium-air battery,
the electrode case is configured by an upper case and a lower case,
an electrode case top wall portion, an electrode case upper inner wall portion, and an electrode case upper outer wall portion are integrally formed in the upper case,
the electrode case top wall portion has annular shape, and covers upper surfaces of the anode, the cathode, and the liquid holder,
the electrode case upper inner wall portion has a cylindrical shape which downward extends from an inner peripheral edge of the electrode case top wall portion along an inner circumferential surface of the cathode, and which covers an upper portion of the inner circumferential surface of the cathode,
the electrode case upper outer wall portion has a cylindrical shape which downward extends from an outer peripheral edge of the electrode case top wall portion along the outer circumferential surface of the anode, and which covers an upper portion of the outer circumferential surface of the anode,
in the lower case, an electrode case bottom wall portion, an electrode case lower inner wall portion, and an electrode case lower outer wall portion are formed integrally with the cover member,
the electrode case bottom wall portion is configured by a part of the cover member opposed to the lower surfaces of the anode and the cathode, covers the lower surfaces of the anode and the cathode, and has the liquid absorber through hole as the liquid absorber extraction port,
the electrode case lower inner wall portion has a cylindrical shape which rises from an inner peripheral edge of the electrode case bottom wall portion along the inner circumferential surface of the cathode, and covers a lower portion of the inner circumferential surface of the cathode,
the electrode case lower outer wall portion has a cylindrical shape which rises from an outer peripheral edge of the electrode case bottom wall portion along the outer circumferential surface of the anode, and covers an lower portion of the outer circumferential surface of the anode,
the upper case and the lower case are integrated with each other in a state where the lower end of the electrode case upper inner wall portion, and the upper end of the electrode case lower inner wall portion are butted against each other, and the lower end of the electrode case upper outer wall portion, and the upper end of the electrode case lower outer wall portion are butted against each other,
the electrode case passingly holds the liquid sucking wick inside the electrode case upper inner wall portion and the electrode case lower inner wall portion, and
the plural air intake ports are disposed at predetermined intervals in the circumferential direction while extending over one or both of the electrode case upper outer wall portion and the electrode case lower outer wall portion.

12. The air improving device according to claim 11, wherein an anode terminal which is fixed in a state where one end side is in contact with the anode, and in a state where another end side is exposed from the upper surface of the upper case, and a cathode terminal which is fixed in a state where one end side is in contact with the cathode, and in a state where another end side is exposed from the upper surface of the upper case are disposed in the upper case, and an anode connection terminal which, when the air improver is mounted into the device body, is elastically contacted with the anode terminal, a cathode connection terminal which, when the air improver is mounted into the device body, is elastically contacted with the cathode terminal, and a control board to which the anode connection terminal, the cathode connection terminal, and the electrical load are electrically connected are disposed in the device body.

* * * * *